United States Patent
Fujii et al.

(10) Patent No.: US 8,115,478 B2
(45) Date of Patent: Feb. 14, 2012

(54) DEVICE AND METHOD FOR MEASURING CONCENTRATION OF MAGNETIC MATERIAL

(75) Inventors: Takashi Fujii, Aioi (JP); Shigeki Kagomiya, Shizuoka (JP)

(73) Assignees: Diesel United, Ltd., Tokyo (JP); Meiyo Electric Co., Ltd., Shizuoka-shi (KR)

( * ) Notice: Subject to any disclaimer, the term of this patent is extended or adjusted under 35 U.S.C. 154(b) by 612 days.

(21) Appl. No.: 12/302,631

(22) PCT Filed: May 29, 2007

(86) PCT No.: PCT/JP2007/000572
§ 371 (c)(1),
(2), (4) Date: Nov. 26, 2008

(87) PCT Pub. No.: WO2007/138746
PCT Pub. Date: Dec. 6, 2007

(65) Prior Publication Data
US 2009/0189599 A1  Jul. 30, 2009

(30) Foreign Application Priority Data
May 30, 2006  (JP) .................. 2006-149383

(51) Int. Cl.
*G01N 27/74* (2006.01)
*G01R 33/12* (2006.01)
(52) U.S. Cl. ........................................ 324/204
(58) Field of Classification Search .................. 324/204
See application file for complete search history.

(56) References Cited

U.S. PATENT DOCUMENTS

| 4,613,815 A | * | 9/1986 | Christel, Jr. ............... 324/233 |
| 4,651,092 A | * | 3/1987 | Brunsch et al. ............ 324/204 |
| 5,001,424 A | * | 3/1991 | Kellett et al. .............. 324/204 |
| 5,493,215 A | | 2/1996 | Otten |
| 5,793,199 A | * | 8/1998 | Kasahara et al. ........... 324/204 |

FOREIGN PATENT DOCUMENTS

| JP | 6 288986 | 10/1994 |
| JP | 7 26758 | 5/1995 |
| JP | 8 9653 | 3/1996 |
| JP | 8 201245 | 8/1996 |
| JP | 10 268013 | 10/1998 |
| JP | 2001 23833 | 1/2001 |
| JP | 2002 296893 | 10/2002 |
| JP | 2003 232776 | 8/2003 |
| JP | 2005 83897 | 3/2005 |
| JP | 2005 299459 | 10/2005 |

* cited by examiner

*Primary Examiner* — Roberto Velez
(74) *Attorney, Agent, or Firm* — Oblon, Spivak, McClelland, Maier & Neustadt, L.L.P.

(57) ABSTRACT

A device for measuring a concentration of magnetic material has exciting coils 11a and an output coil 11b which generates exciting voltage when alternating current flows through the exciting coils 11a. Measurement means 6 is provided to measure variation in phase difference between voltages of the exciting and output coils 11a and 11b, so that a concentration of magnetic material is measured with high accuracy from variation in phase difference when a test object is caused to approach the exciting coil 11a or/and the output coil 11b. A minute concentration of magnetic material in the fluid is continuously measured.

13 Claims, 12 Drawing Sheets

DEVICE AND METHOD FOR MEASURING CONCENTRATION OF MAGNETIC MATERIAL

TECHNICAL FIELD

The present invention relates to a device and a method for measuring a concentration of magnetic material.

BACKGROUND ART

In an engine or other prime mover with piston or other reciprocating parts, for example, the piston and a cylinder will wear due to relative sliding motions between them, resulting in production of iron powder or other magnetic material entrained in drain oil from the engine flowing through a passage. Thus, it is required to measure a concentration of magnetic material contained in the passage of the drain oil from the engine in order to accurately grasp worn degree of the equipment.

Generally, in order to grasp the worn degree of the equipment, the fluid such as lubricant or drain oil is manually sampled to measure a concentration of magnetic material through chemical technique; alternatively, a device for measuring a concentration of magnetic material is arranged adjacent to the passage of flow of the fluid to measure the concentration of magnetic material.

The device for measuring a concentration of magnetic material comprises, for example, magnetic-field applying means and magnetic measurement means with a magnetic sensor in the form of a superconducting quantum interference device both arranged adjacent to the passage of flow of the fluid such as drain oil so as to detect only magnetic fields of magnetized components. This has been disclosed for example in Patent Literature 1. Another example comprises an observational LC oscillation circuit with a first coil adjacent to the passage of the fluid and a corrective LC oscillation circuit with a second coil arranged in a position not affected by magnetic material in the fluid, the concentration of magnetic material being detected on the basis of difference in oscillating frequency between the observation and corrective LC oscillation circuits. This has been disclosed for example in Patent Literature 2.
[Patent Literature 1] JP10-268013A
[Patent Literature 2] JP2005-83897A

SUMMARY OF INVENTION

Technical Problems

However, there has been a problem that a concentration of magnetic material cannot be measured with high accuracy by the conventional method using the chemical technique, detection only of the magnetic fields of the magnetized components or mere difference between the oscillating frequencies. Further, the manual sampling of the fluid such as lubricant or drain oil to measure the concentration of magnetic material is troublesome and is defective in that measurement can be effected only in a constant time interval. Use of the conventional device for measuring the concentration of magnetic material may cause disturbances and have difficulty in continuous measurement with high accuracy due to accumulated solid matters and/or variation in flow rate of the fluid. In use of any other conventional device for measuring the concentration of magnetic material, it has been requested in vain to measure a minute concentration of magnetic material with high accuracy through enhanced reduction of noises.

The invention was made in view of the above and has its object to provide a device and a method for measuring a concentration of magnetic material which measure a concentration of magnetic material with high accuracy and which continuously measure a minute concentration of magnetic material contained in fluid.

Solution to Problems

The invention is directed to a device for measuring a concentration of magnetic material with an exciting coil and an output coil for generating exciting voltage when an alternating current flows through said exciting coil, comprising measurement means for measuring variation in phase difference between voltages of said exciting and output coils, the concentration of magnetic material being grasped from said variation in phase difference generated upon approaching of a test object to said exciting coil or/and said output coil.

In the invention, preferably, a lock-in amplifier is used as said measurement means.

In the invention, preferably, voltage of said exciting coil is used as reference signal for said lock-in amplifier.

In the invention, it is preferable that, as means for causing the test object to approach said exciting coil or/and output coil, drive means is provided which introduces the test object from a passage of flow of or a pool for pooling of the fluid containing magnetic material.

The invention is directed to a device for measuring a concentration of magnetic material comprising a detection unit connected to a passage of flow of or a pool for pooling of fluid containing magnetic material and having inflow/outflow guide means and detection means, and a signal processing unit connected to said detection means and having a lock-in amplifier, said detection unit guiding inflow/outflow of the fluid by means of the inflow/outflow guide means and obtaining a detection signal of magnetic material with the fluid being introduced and a corrective detection signal with the fluid being discharged from an output signal indicative of AC voltage through the detection means, said signal processing unit employing reference signals with the same frequencies as those of the respective signals to noise-remove said respective signals through the lock-in amplifier and detecting phase differences between said respective signals and the reference signals to thereby conduct conversion into DC voltage signals depending on detected phase difference amount, difference of respective values after conversion being detected as concentration of magnetic material.

The invention is directed to a device for measuring a concentration of magnetic material comprising a detection unit connected to a passage of flow of or a pool for pooling of fluid containing magnetic material and having inflow/outflow guide means and detection means and a signal processing unit connected to said detection means and having a lock-in amplifier, said detection unit guiding inflow/outflow of the fluid through the inflow/outflow guide means and obtaining a detection signal of magnetic material with the fluid being introduced and a corrective detection signal with the fluid being discharged through the detection means, said signal processing unit using reference signals of the same frequencies as those of the respective signals to conduct noise removal of said respective signals through the lock-in amplifier and then conducting conversion into DC voltage signals, difference of the respective values after conversion being detected as concentration of magnetic material.

In the invention, it is preferable that said signal processing unit shifts the phase of the reference signal or the detection signal of magnetic material such that value of the output signal converted into DC voltage signal approaches substantially zero when no magnetic material is detected.

In the invention, it is preferable that said detection means comprises an exciting coil and an output coil for obtaining detection signal of magnetic material, an output signal for AC voltage being generated in the output coil by application of AC voltage to said exciting coil, a detection signal for magnetic material or a corrective detection signal being obtained from said output signal, reference signal being obtained from an oscillating circuit connected to said exciting coil.

In the invention, it is preferable that said detection means comprises a plurality of exciting coils wound inversely to each other, a detection coil being arranged between the plural exciting coils such that an output signal of said detection coil is small.

In the invention, it is preferable that said inflow/outflow guide means guides the fluid through reciprocal movements of the piston.

In the invention, it is preferable that obtained from the test object or fluid containing magnetic material is at least one of informations including concentration, rate of change in concentration, amplitude of variations of concentration, cycle of variations of concentration and concentration deflection in multipoint measurement of magnetic material, status of sliding parts being determined on the basis of preliminarily obtained correlationship between concentration of magnetic material and status of sliding parts.

In the invention, preferably, alert means is provided which issues a warning or/and alert depending on status of sliding parts.

In the invention, it is preferable that depending upon the status of the sliding parts, amount, timing, pressure, temperature and/or injection method of lubricating fluid to be supplied to the sliding parts and/or properties of the lubricating fluid are controlled.

The invention is directed to a method for measuring a concentration of magnetic material using an exciting coil and an output coil for generating exciting voltage when alternating current flows through said exciting coil, which comprises measuring variation in phase difference between voltages of said exciting and output coils upon approaching of test object to said exciting coil or/and output coil, thereby grasping concentration of magnetic material.

In the invention, it is preferable that the voltage signal of said output coil is partly phase-inversed and is converted into DC for measurement of variation in phase difference.

In the invention, it is preferable that the voltage signal of said output coil is partly phase-inversed, using the voltage signal of said exciting coil.

In the invention, it is preferable that said test object is introduced from a passage of flow of or a pool of the fluid containing magnetic material and is caused to approach said exciting coil or/and output coil.

The invention is directed to a method for measuring a concentration of magnetic material comprising processing with the fluid being introduced wherein fluid is introduced from a passage of flow of or a pool for pooling of fluid containing magnetic material into a detection unit and a detection signal is obtained from the fluid in the detection unit while preparing a reference signal with the same frequency as that of the detection signal, noise removal being conducted by a lock-in amplifier where the detection signal for magnetic material is combined with the reference signal with the same frequency, conversion being conducted into DC voltage signal as output value for concentration of magnetic material, processing with the fluid being discharged wherein the corrective detection signal is obtained from the detection unit with the fluid being discharged therefrom while the reference signal of the same frequency is prepared, noise removal being conducted by the lock-in amplifier with the corrective detection signal being combined with the reference signal of the same frequency, conversion being conducted into DC voltage signal as comparative output value, said output value for concentration of magnetic material being corrected by said comparative output value.

In the invention, it is preferable that during processing with the fluid being introduced and processing with the fluid being discharged, detection signal for magnetic material and corrective detection signal are obtained from output signal indicative of AC voltage, noise removal being conducted by the lock-in amplifier from said respective signals with the detection signal for magnetic material and the corrective detection signal and the reference signal of the same frequency being combined together while phase differences between said respective signals and the reference signals and effective values of said signals are detected, conversion being conducted into output value for concentration of magnetic material and comparative output value depending on detected phase difference amount.

In the invention, it is preferable that the processing with the fluid being introduced and the processing with the fluid being discharged are alternately and continuously repeated so that the difference is further converted into DC voltage signal from the output value for concentration of magnetic material and the comparative output value, said difference being converted into concentration of magnetic material by preliminarily obtained correlationship to eliminate measurement errors due to disturbance and changes over time (moment-to-moment changes).

In the invention, it is preferable for obtaining maximum amplification in a succeeding amplifier that the phase of said reference signal or the phase of the detection signal for magnetic material is shifted and the value of the output signal of the signal processor converted into DC voltage signal is made to approach zero.

In the invention, it is preferable, from a viewpoint of always ascertaining through self-diagnosis of the device the measurement conducted in proper conditions, that obtained from the test object or fluid containing magnetic material is at least one of informations including concentration, rate of change in concentration, amplitude of variations of concentration, cycle of variations of concentration and concentration deflection in multipoint measurement of magnetic material, status of sliding parts being determined on the basis of preliminarily obtained correlationship between concentration of magnetic material and status of sliding part.

In the invention, it is preferable, from a viewpoint of always ascertaining the measurement conducted in proper conditions, that a warning or/and an alert is issued depending on status of the sliding parts.

In the invention, it is preferable that depending on status of the sliding parts, amount, timing, pressure, temperature and injection method of the lubricating fluid to be supplied to the sliding parts and properties of the lubricating fluid are controlled.

Thus, according to the invention, voltages of the exciting and output coils generated depending on concentration of magnetic material and phase difference of the signals are utilized; such voltages and variation of phase difference can be sensitively measured by causing the test object containing magnetic material to approach the exciting coil or/and output coil. Thus, concentration of magnetic material can be measured with high accuracy. The invention utilizes phase difference between the voltages of the exciting and detection coils and variation in voltage of the output coil, can comprehensively grasp various variations such as variation in reactance of the exciting coil depending on whether magnetic material is present or not, variation in reactance of the output coil depending on whether magnetic material is present or not, variation of eddy current generated in the test object, variation in joule loss due to eddy current, variation in eddy current produced in objects surrounding the coils and variation in joule loss due to eddy current so that the concentration of magnetic material can be measured with high accuracy.

According to the invention, the detection signal of magnetic material is obtained from the fluid in the detection unit while preparing the reference signal having the same frequency as that of the exciting voltage, variation of phase difference relative to the reference signal and voltage variation of the output coil being measured, conversion being made into DC voltage signal depending on measured phase difference amount. Then, the corrective detection signal in the detection unit is obtained from the detection unit with the fluid being discharged; phase difference with the reference signal is measured, and conversion is made into DC voltage signal depending on measured phase difference amount, the difference between the converted values with the fluid being introduced and discharged being used as concentration of magnetic material. As a result, phase difference variation and voltage variation of the output coil can be utilized to measure the concentration of magnetic material with extremely high accuracy. The variation of phase difference and voltage variation of the output coil are finally converted into effective value of voltage and used as detection signal of magnetic material.

According to the invention, the detection signal of magnetic material obtained from the fluid in the detection unit is noise-removed by the band-pass filter while preparing the reference signal having the same frequency as that of the exciting voltage, and further noise-removed in combination with the reference signal, conversion being made into DC voltage component part for concentration of magnetic material. Then, the corrective detection signal obtained from the detection unit with the fluid being discharged is noise-removed in combination with the reference signal, conversion being made into comparative DC voltage component part, the difference between the respective DC component parts after conversion being used as concentration of magnetic material in the fluid. As a result, noise superimposed on the output signal upon measurement is removed and the accumulated solid matters are discharged by guided inflow/outflow of the fluid, so that minute concentration of magnetic material in fluid can be measured with high accuracy.

The guided inflow and outflow of the fluid is repeated in batches to obtain difference in respective measured values in plural times, so that the data for the plural butches are processed to always eliminate measurement errors due to changes over time, so that minute concentration of magnetic material in fluid can be continuously measured.

In the invention, the detection signal for magnetic material with the fluid being introduced and the corrective detection signal with the fluid being discharged are obtained from the output signal indicative of AC voltage, and phase differences between said respective signals and the reference signals are detected, conversion being made into DC voltage signal depending on detected phase difference amount. Thus, slight phase differences can be obtained as large output values and concentration of magnetic material can be measured highly sensitively, so that minute concentration of magnetic material in fluid can be favorably measured with high accuracy.

Advantageous Effects of Invention

As mentioned in the above, the invention which utilizes phase difference has excellent effect or advantage that a concentration of magnetic material can be continuously measured with high accuracy.

Figure 1:
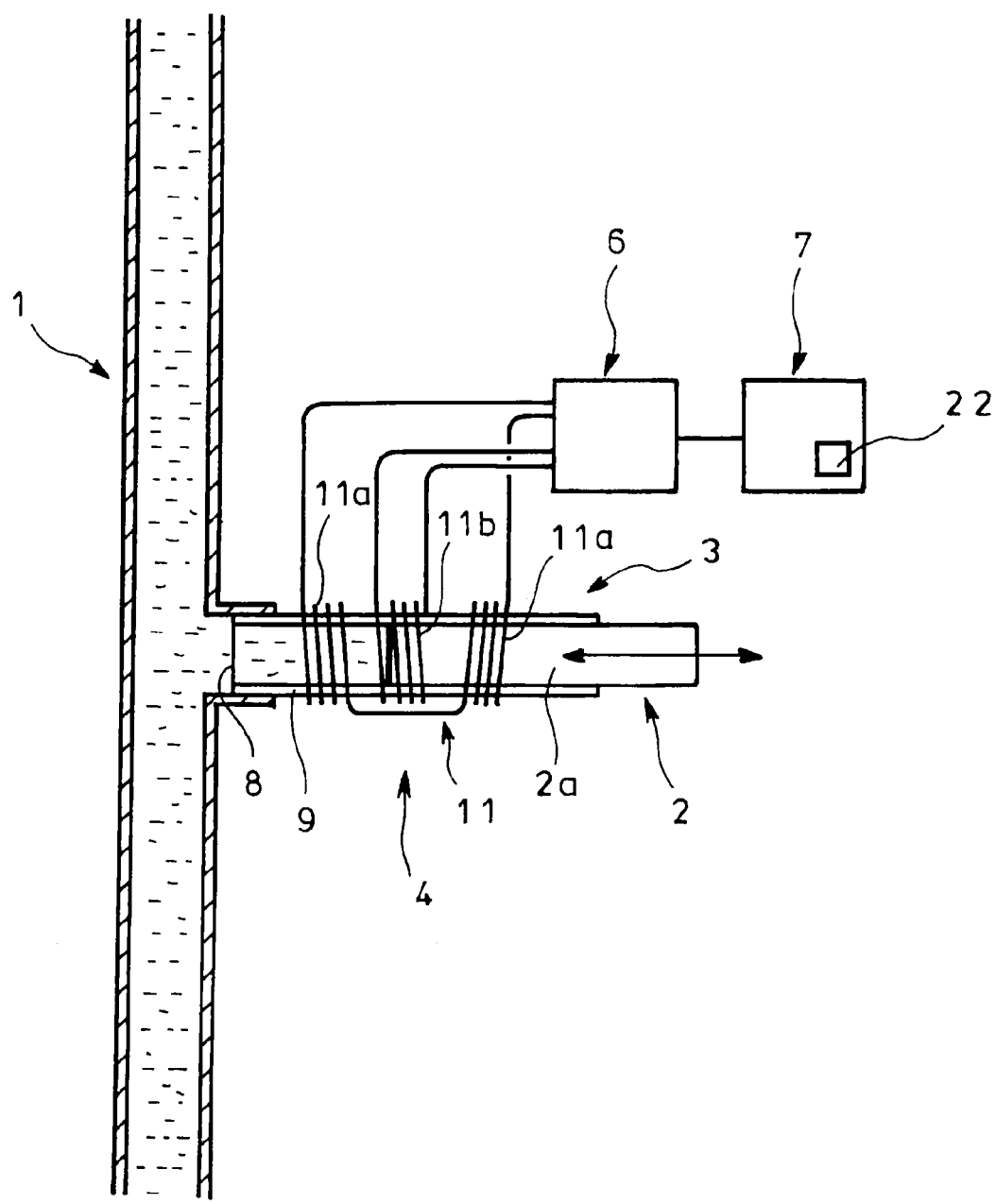
FIG. 1 is a schematic view showing a first embodiment of the invention.

REFERENCE SIGNS LIST 1 passage
2 inflow/outflow guide means (drive means)
2a piston
3 detection means
4 detection unit
5 signal processor
6 signal processing unit (measurement means)
7 measured value indicating and abnormality determination device (alert means)
11 coil
11a exciting coil
11b detection coil (output coil)
11c exciting coil
11d detection coil (output coil)
14 sine wave oscillating circuit (oscillating circuit)
31 passage
32 inflow/outflow guide means
32a piston
33 detection means
34 detection unit
35 lock-in amplifier
36 signal processing unit 37 measured value indicating and abnormality determination device (alert means)
46 coil
46a exciting coil
46b detection coil (output coil)
49 sine wave oscillating circuit (oscillating circuit)
61 passage
70 second pool

DESCRIPTION OF EMBODIMENTS

A first embodiment of a device and a method for measuring a concentration of magnetic material according to the invention will be described. FIGS. 1-8 show the first embodiment.

In the first embodiment, connected to a conduit passage 1 of flow of fluid such as drain oil containing magnetic material powder is a detection unit 4 comprising inflow/outflow guide means (drive means) 2 and detection means 3. Connected to the detection means 3 in the detection unit 4 is a signal processing unit (measurement means) 6 with a signal processor 5, the signal processing unit 6 being connected to a measured value indicating and abnormality determination device 7.

The conduit passage 1 extends linearly and horizontally for inflow and outflow of the lubricant to and from an equipment (not shown) with sliding parts or components. The conduit passage 1 is not limited to the passage extending linearly and horizontally; it may be a passage extending curvedly, a passage extending angularly, a passage extending vertically or a passage extending obliquely. The fluid is not limited to lubricant; it may any fluid. The sliding parts are not limited to a drive piston and a drive cylinder; they may be any, provided that they are slidable.

The detection unit 4 comprises a cylindrical detection body 9 associated with the passage 1 through an opening 8, a piston 2a as inflow/outflow guide means 2 which slides within the detection body 9 to guide inflow and outflow of lubricant (detection fluid), a rotary part 10 as drive means for reciprocating the piston 2a and coils 11 as detection means 3 arranged on an outer periphery of the detection body 9.

The coils 11 comprise two exciting coils 11a wound inversely and connected in series to each other and a detection coil (output coil) 11b arranged between and adjacent to the exciting coils 11a, an output signal indicative of AC voltage (exciting voltage) being generated in the detection coil 11b when the AC voltage is applied to the exciting coils 11a. The exciting and detection coils 11a and 11b are adjusted to have substantially uniform mutual inductance by adjusting wound number of and distance between the coils 11. Both of the coils 11a and 11b have no limitation in their numbers. Preferably, a shield such as an aluminum cylinder is arranged outwardly of the coils 11 so as to prevent intrusion of any outside noises.

Figure 2:
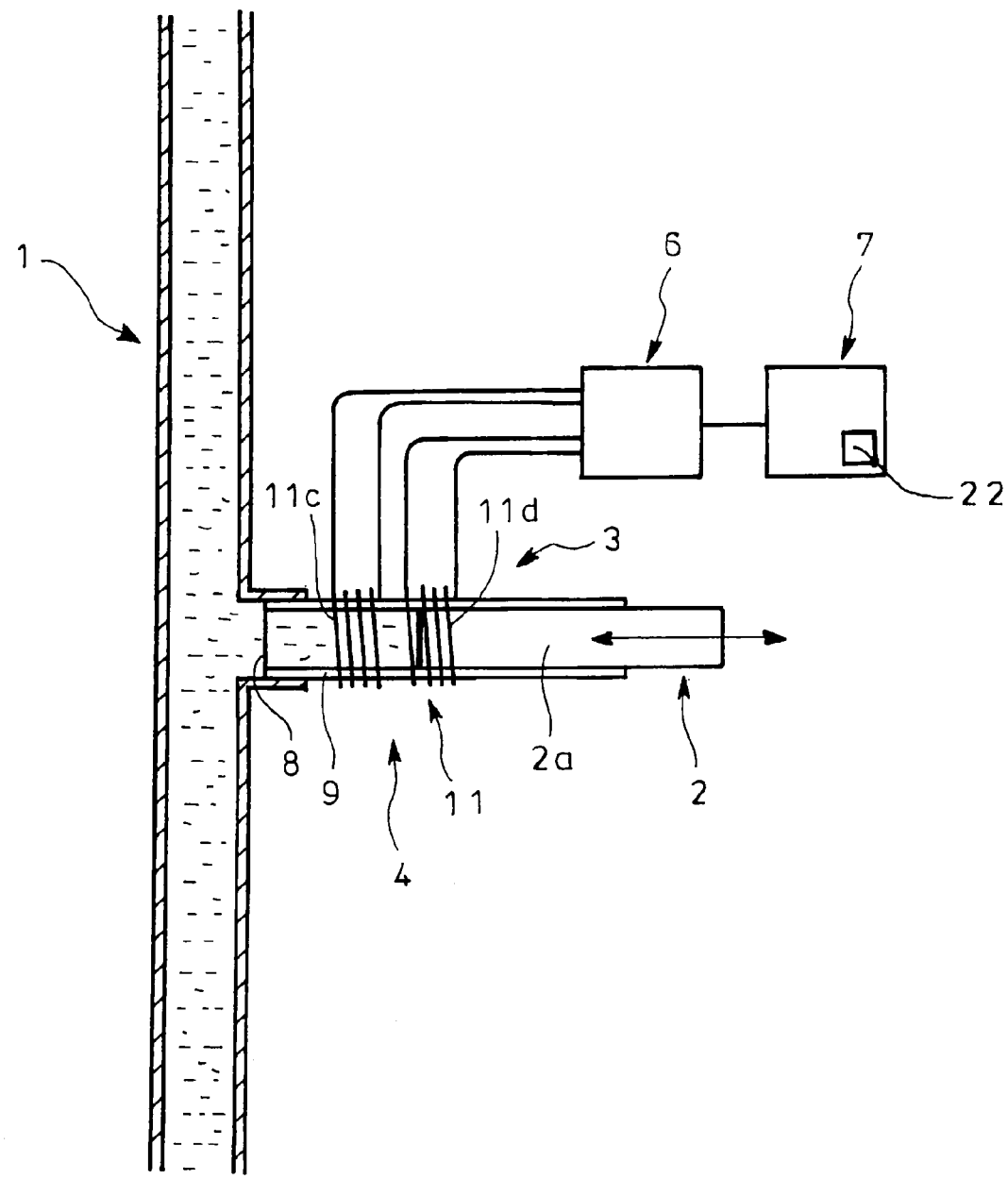
FIG. 2 is a schematic view showing a variation of the first embodiment.

Alternatively, as shown in FIG. 2, the coils 11 of the detection means 3 may comprise an exciting coil 11c and a detection coil (output coil) 11d arranged adjacent to the exciting coil 11c. Also in this case, when AC voltage is applied to the exciting coil 11c, an output signal indicative of the AC voltage (exciting voltage) is generated in the detection coil 11d, adjustment being made such that the output signal indicative of the AC voltage (exciting voltage) in the detection coil 11d is small when no magnetic material is detected.

Figure 3:
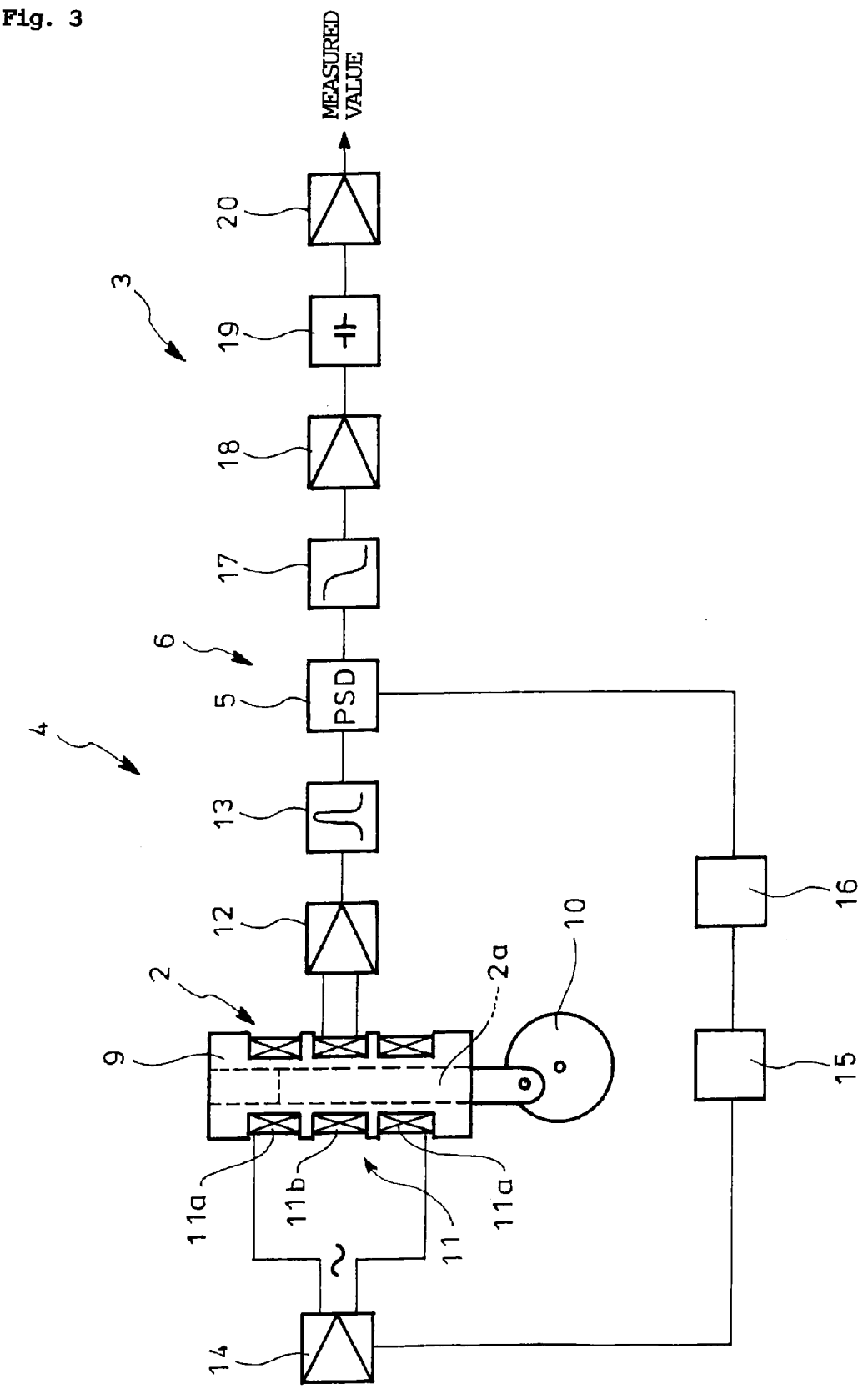
FIG. 3 is a block diagram showing inflow/outflow guide means and a signal processing unit according to the embodiment.

In order to obtain detection signal of magnetic material or corrective detection signal from the output signal of the detection coil 11b, the signal processing unit 6 comprises, as shown in FIG. 3, an amplifier circuit 12 connected to the detection coil 11b to amplify a faint wave signal, a band-pass filter 13 connected to the amplifier circuit 12 to remove noises of the wave signal in a predetermined range, a sine wave oscillating circuit 14 for obtaining sine wave for excitation, a phase circuit 15 connected to the oscillating circuit 14 to shift the phase of the sine wave and an edge-triggered circuit 16 connected to the phase circuit 15 to convert the sine wave into a rectangular wave.

It is preferable that, upon setting or adjustment and with no magnetic material being detected, the phase circuit 15 shifts the phase by 10°-170°, preferably by 45°-135°, further preferably by about 90°. The phase shift may be slightly over or below due to electric deviance. The phase circuit 15 may be alternatively positioned between the band-pass filter 13 and the signal processor 5 to shift not the reference signal, but the detection signal of magnetic material or corrective detection signal. The signal processor 5 is preferably a lock-in amplifier; however, it may be any, provided that it can measure the variation in phase difference.

Figure 4:
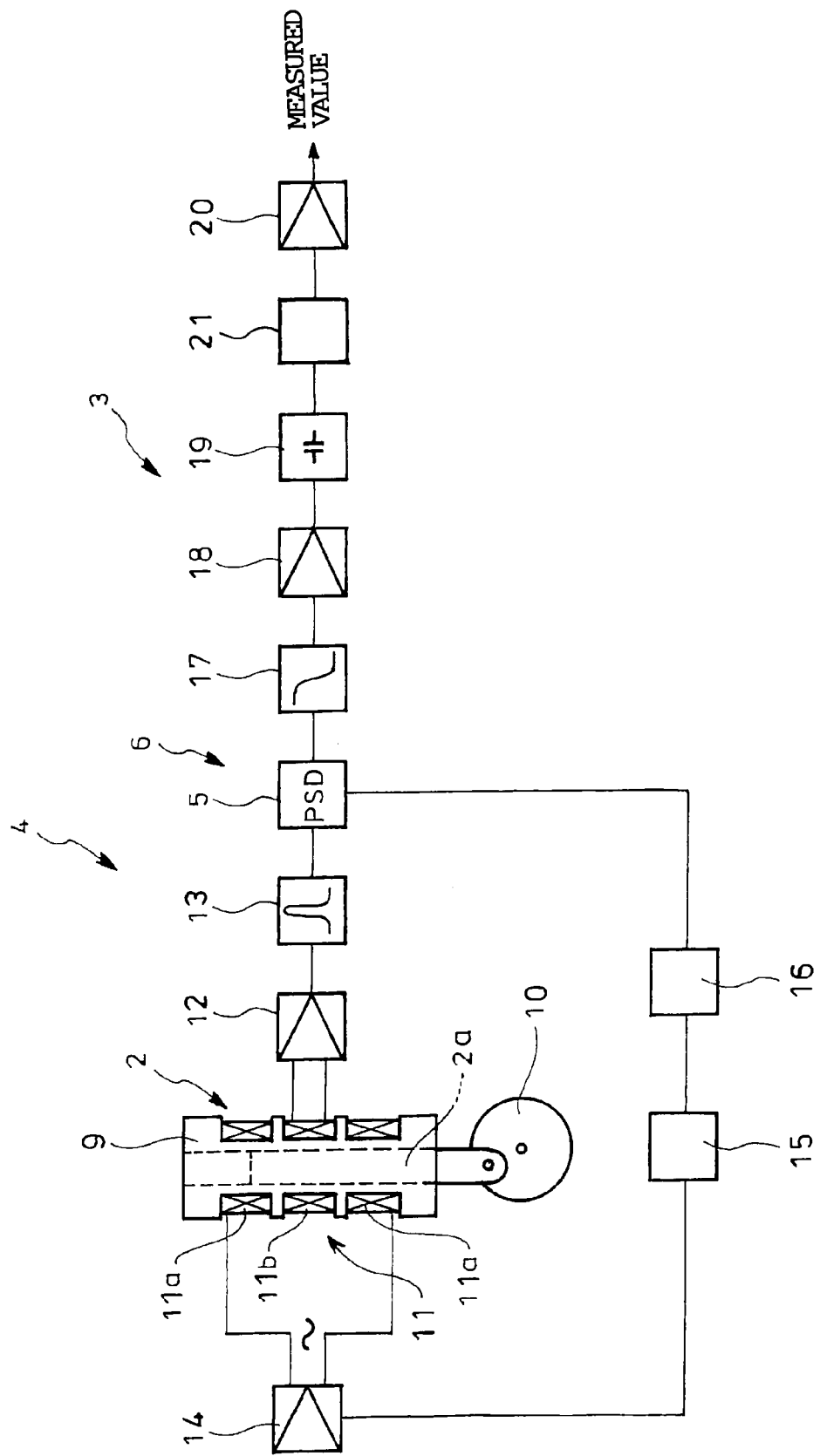
FIG. 4 is a block diagram showing the inflow/outflow guide means and a variation of the signal processing unit according to the embodiment of the invention.

The signal processing unit 6 comprises a signal processor 5 connected to the band-pass filter 13 and to the edge-triggered circuit 16, a low-pass filter 17 connected to the signal processor 5 to convert the output signal into a DC voltage signal, an amplifier 18 connected to the filter 17 to amplify the DC voltage signal, an AC signal transmission circuit 19 connected to the amplifier 18 to transmit only a varied amount of the DC voltage signal through the guided inflow and outflow of the detection fluid and an amplifier 20 connected to the transmission circuit 19. A DC conversion circuit 21 for conversion of the AC signal in accordance with the movement of the piston 2a into a DC signal may be provided, as shown in FIG. 4, between the AC signal transmission circuit 19 and the amplifier 20 for facilitation of succeeding processing.

Further, the measured value indicating and abnormality determination device 7 is connected, as shown in FIGS. 1-4, to the amplifier 20 of the signal processing unit 6 for conversion of the signal into a value of concentration of magnetic material, and accommodates therein a controller 22 for predetermined controls to make, for example, lubrication control or issue of abnormality alert on the lubrication status of the sliding parts.

Mode of operation of the first embodiment according to the invention will be described.

When the concentration of magnetic material powder contained in the lubricant (fluid) is to be measured, the piston 2a as inflow/outflow guide means 2 is drawn to introduce the lubricant from the passage 1 into the detection unit 4 where the output signal is measurement processed with the lubricant being present. Preferably, the piston 2a is drawn to introduce the lubricant or drain oil to an extent that the fluid reaches the one of the exciting coils 11a and a half of the detection coil 11b.

Figure 6:
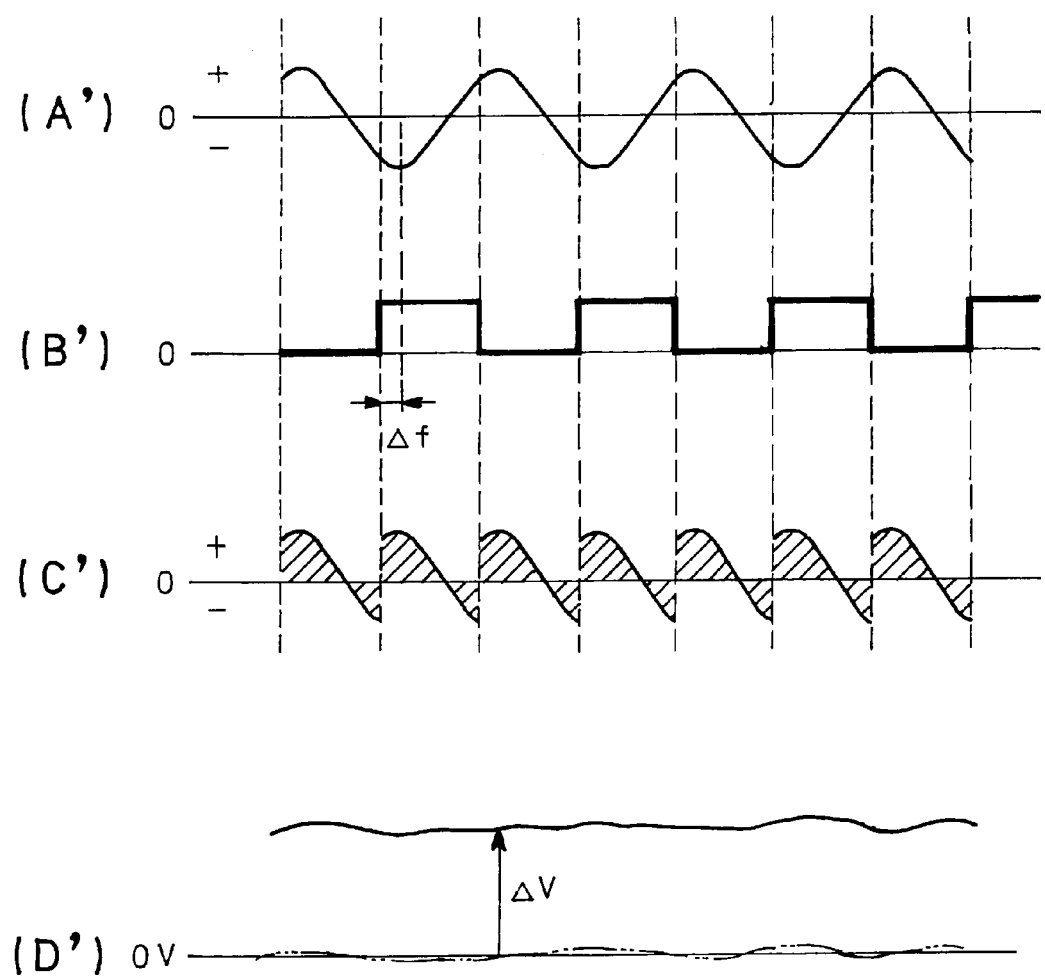
FIG. 6 is a conceptual diagram showing processing from output signal to output value (DC voltage signal) for concentration of magnetic material in condition influenced by magnetic material.

When the measurement processing is conducted with the lubricant or drain oil being in the detection unit 4 (i.e., during processing with the fluid being introduced), the detection signal for magnetic material is obtained ((A') in FIG. 6) from the lubricant or drain oil in the detection unit 4 by the detection coil 11b, the amplifier circuit 12 and the band-pass filter 13 while preparing a reference signal ((B') in FIG. 6) which has the rectangular wave and which has the same frequency as that of the exciting voltage with a constant phase difference through shift of the phase with a predetermined angle by the exciting coil 11a, the sine wave oscillating circuit 14, the phase circuit 15 and the edge-triggered circuit 16. Noise removal is conducted by the signal processor 5 in combination with the reference signal and the phase difference is detected between the detection signal of magnetic material and the reference signal and converted by the low-pass filter 17 into plain DC voltage signal ((D') in FIG. 6) as output value for the concentration of magnetic material and is inputted via the amplifier 18 into the AC signal transmission circuit 19. In (B') of FIG. 6, the setting is made with the phase shift being about 90°; (C') of FIG. 6 shows the detection signal for magnetic material with inversions by the reference signal, such areas being integration converted into (D') of FIG. 6.

Then, the piston 2a as inflow/outflow guide means 2 is pushed out to discharge (effect guided outflow of) the lubricant in the detection unit 4; then, the output signal with no lubricant being present (i.e., of the inflow/outflow guide means 2 itself) is measurement processed. Time interval of reciprocal movements of the inflow/outflow guide means 2, which may vary depending on for example viscosity of the fluid to be measured, is preferably several seconds.

Figure 5:
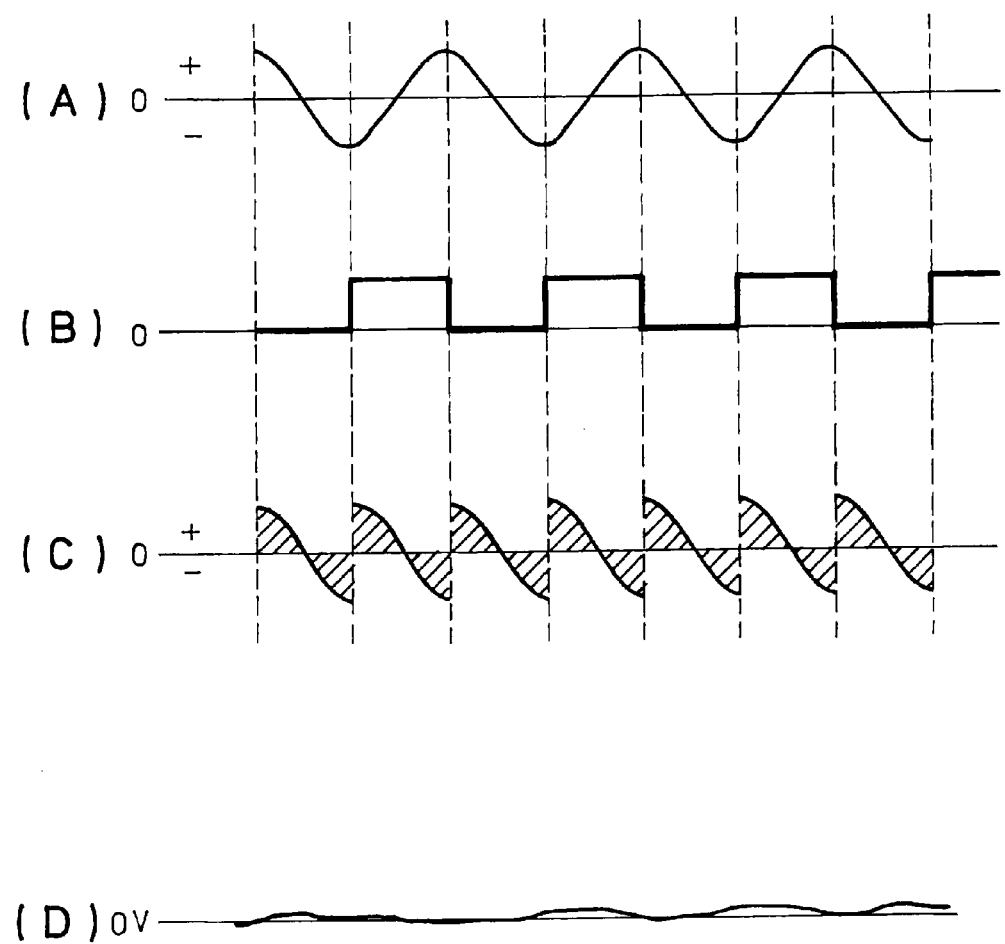
FIG. 5 is a conceptual diagram showing processing from output signal to comparative output value (DC voltage signal) in condition with no influence by magnetic material.

When the measurement processing is conducted with the lubricant or drain oil being discharged (guided to make outflow) out of the detection unit 4 (i.e., during processing with the fluid being discharged), the corrective detection signal is obtained ((A) in FIG. 5) from the detection unit 4 by the detection coil 11b, the amplifier circuit 12 and the band-pass filter 13 while preparing a reference signal ((B) in FIG. 5) which has the rectangular wave and which has the same frequency as that of the exciting voltage with a constant phase difference through shift of the phase with a predetermined angle by the exciting coil 11a, the sine wave oscillating circuit 14, the phase circuit 15 and the edge-triggered circuit 16. Noise removal is conducted by the signal processor 5 in combination with the reference signal and the phase difference is detected between the corrective detection signal and the reference signal and is converted by the low-pass filter 17 into plain DC voltage signal ((D) in FIG. 5) as comparative output value and is inputted via the amplifier 18 into the AC signal transmission circuit 19. In (B) of FIG. 5, the setting is made with the phase being about 90°; (C) of FIG. 5 shows the detection signal for magnetic material with inversions by the reference signal, such areas being integration converted into (D) of FIG. 5.

In order to correct the output value for concentration of magnetic material, as shown in FIG. 6, difference $\Delta V$ is obtained by the AC signal transmission circuit 19 from the output value for concentration of magnetic material and the comparative output value and is converted into a value of concentration of magnetic material by the measured value indicating and abnormality determination device 7, using preliminarily obtained correlationship with concentration (functional processing). As to the output value (DC voltage signal) for concentration of magnetic material and the comparative output value (DC voltage signal), phase difference $\Delta f$ between the output signal for magnetic material and the reference signal therefor and phase difference (not shown) between the corrective output signal and the reference signal therefor may be alternatively detected by the signal processor 5 and conversion is made depending upon the detected phase difference amount.

Then, the piston 2a as inflow/outflow guide means 2 is continuously reciprocated to alternately and continuously repeat measurement processing with the lubricant being introduced into the detection unit 4 (processing with the fluid being introduced) and measurement processing with the lubricant being discharged (guided to make outflow) from the detection unit 4 (processing with the fluid being discharged), difference signals are detected by the AC signal transmission circuit 19 and the like from the output values for concentration of magnetic material and the comparative output values, and moving average processing is conducted to obtain an average of the concentrations of magnetic material through the measured value indicating and abnormality determination device 7. The outputs for the concentrations of magnetic material are, as shown in (D') of FIG. 5, AC signals which are above and blow the comparative output value through reciprocal movements of the inflow/outflow guide means 2. Such AC signals may be converted into DC signals, using the DC conversion circuit 21.

Figure 7:
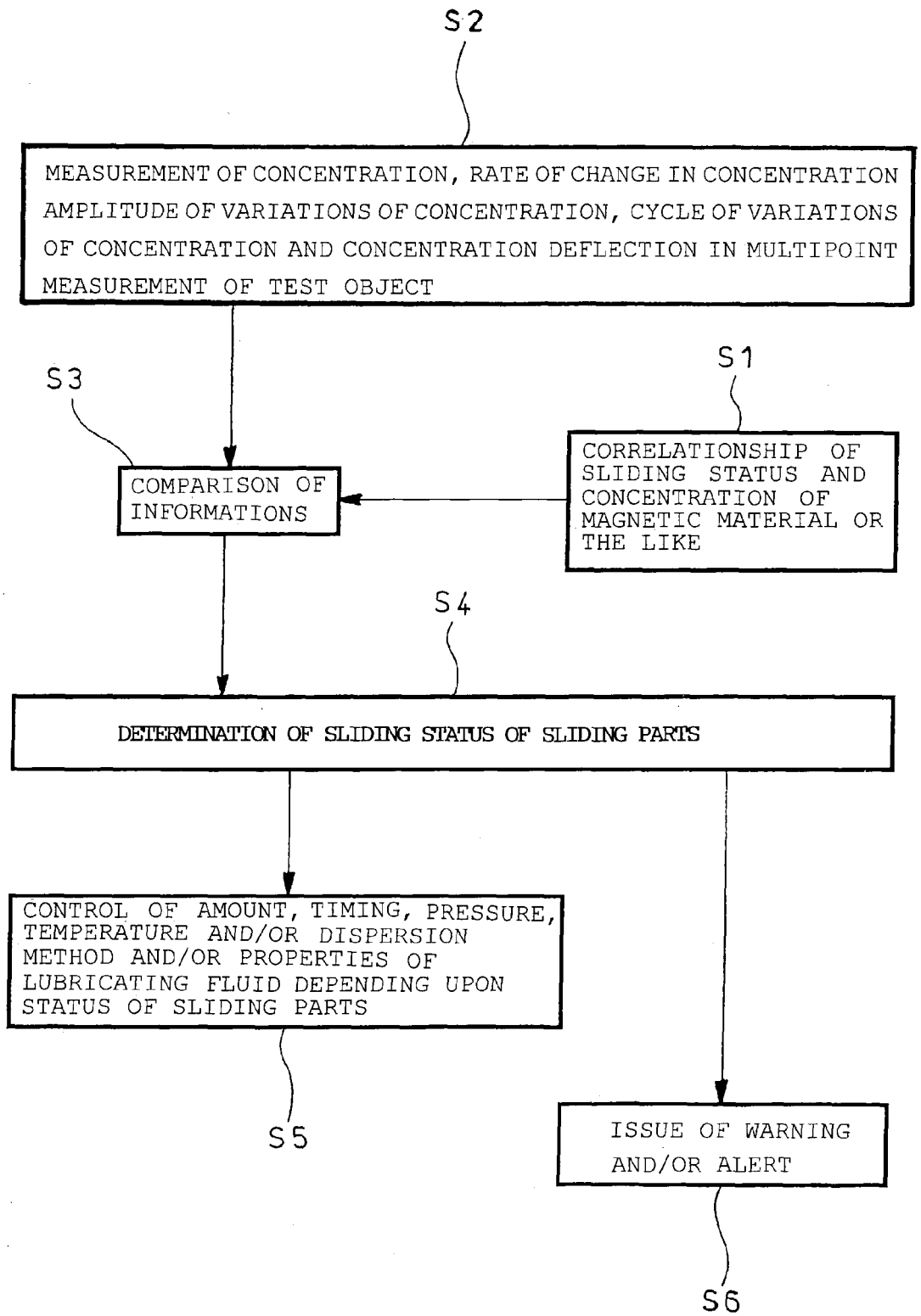
FIG. 7 is a flowchart for determination of sliding status of sliding objects from concentration and the like of magnetic material (test object)

By the controller 22 in the measured value indicating and abnormality determination device 7 as shown in FIG. 7, the correlationship (reference data) of the sliding status of the piston or other sliding parts in the prime mover with the concentration of magnetic material is preliminarily inputted (step S1) while at least one of informations including concentration of magnetic material, rate of change in concentration of magnetic material, amplitude of variations in concentration of magnetic material, cycle of variations in concentration of magnetic material and concentration deflection in multipoint measurement is obtained by the signal processing unit 6 and the like from the fluid (test object) containing magnetic material (step S2). Then, correlationship (reference data) is compared with information obtained from the fluid containing magnetic material (test object) (step S3), so that the sliding status of the piston or other sliding parts is determined (step S4); based on the sliding status of the piston or other sliding parts, amount, timing, pressure, temperature and/or injection method of drain oil (lubricating fluid) to be supplied to the sliding parts and/or properties of the drain oil (lubricating fluid) are controlled (step S5). When the concentration of magnetic material powder exceeds a predetermined value and it is determined that the sliding parts such as piston has considerably worn amount, the fact that it is time for maintenance required is notified to a manager by the measured value indicating and abnormality determination device 7 through warning display, alarm and/or hazard light (step S6).

Thus, the first embodiment uses phase difference between the voltages of the exciting and detection (output) coils 11a and 11b as well as variation in phase difference depending on the concentration of magnetic material upon approaching of the test object containing magnetic material to the exciting coil 11a or/and output coil 11b, so that the concentration of magnetic material can be measured with high accuracy. The first embodiment, which utilizes phase difference between the voltages of the exciting and detection coils 11a and 11b and variation in voltage of the output coil 11b, can comprehensively grasp various variations such as variation in reactance of the exciting coil 11a depending on whether magnetic material is present or not, variation in reactance of the detection coil (output coil) 11b depending on whether magnetic material is present or not, variation of eddy current generated in the test object, variation in joule loss due to eddy current, variation in eddy current produced in objects surrounding the coils and variation in joule loss due to eddy current, and the concentration of magnetic material can be measured with high accuracy. For measurement of the concentration of magnetic material, when phase differences in part of variations were used among variations including variation in reactance of the exciting coil 11a depending on whether magnetic material is present or not, variation in reactance of the detection coil (output coil) 11b depending on whether magnetic material is present or not, variation in eddy current generated in the test object, variation in joule loss by eddy current, variation in eddy current generated in objects surrounding the coil and variation in joule loss by eddy current, affections would be caused by the remaining variations unlike the case of phase difference of voltages, failing in measurement of the concentration of magnetic material with high accuracy.

Figure 8:
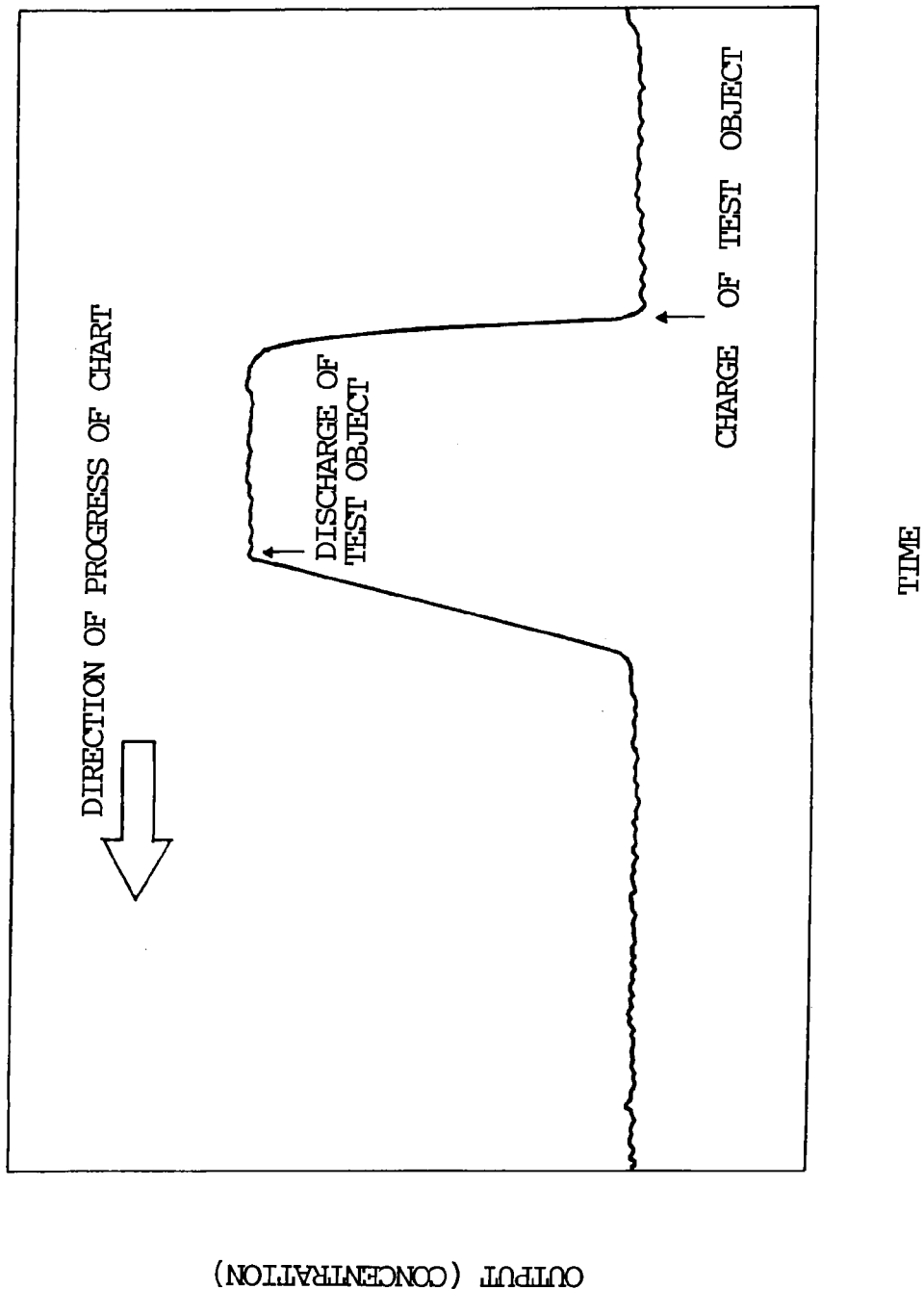
FIG. 8 is a graph showing detected condition when the test object is actually measured.

In fact, results of experiments conducted by the inventors on measurement of fluid (test object) containing several hundreds ppm of iron powder in the embodiment reveal, as shown by the graph of FIG. 8, that the output (concentration) rises instantly upon charge of test object and lowers along with discharge of the test object. It clearly demonstrates that the invention has clear and quick response to magnetic material and can measure the concentration of magnetic material with high accuracy.

In the first embodiment, when the lock-in amplifier of the signal processor 5 is used as measurement means, the lock-in amplifier detects phase difference between the detection signal for magnetic material and the reference signal while conducting noise removal, conversion being made into a signal depending on detected phase difference amount, so that, even in a case of faint phase difference, the concentration of magnetic material is measured highly sensitively and minute concentration of magnetic material in the lubricant can be favorably measured with high accuracy.

In the first embodiment, when voltage of the exciting coil 11a is used as the reference signal for the lock-in amplifier 1, the detection signal of magnetic material with the lubricant being introduced and the corrective detection signal with the lubricant being discharged are obtained from the output signal indicative of AC voltage, so that phase difference is easily detected by the lock-in amplifier while noise removal is conducted, minute concentration of magnetic material in the lubricant can be favorably measured with high accuracy.

In the first embodiment, when the driven means for introducing the test object from the passage for flow of or the pool for pooling of the fluid containing magnetic material is provided as the means for causing the test object to approach the exciting coil 11a or/and output coil 11b, the fluid test object is readily obtained or discharged, so that a minute concentration of magnetic material in the lubricant can be continuously measured with high accuracy.

According to the first embodiment, the detection signal of magnetic material is obtained from the fluid in the detection unit 4 while preparing the reference signal of the same frequency, variation of phase difference relative to the reference signal and voltage variation of the output coil 11b are measured, conversion being made into signal depending on measured phase difference amount. Then, the corrective detection signal in the detection unit 4 is obtained from the detection unit 4 with the fluid being discharged; variation of phase reference relative to the reference signal is measured, conversion being made into signal depending on measured phase difference amount; and difference between the converted values with the fluid being introduced and discharged is used as concentration of magnetic material. As a result, variation of phase difference, and voltage variation of the output coil 11b can be utilized to measure the concentration of magnetic material with extremely high accuracy. The variation of phase difference and voltage variation of the output coil 11b are finally converted into effective voltage value and used as detection signal of magnetic material.

For the concentration of magnetic material, variation in a batch of guided inflow and outflow of the lubricant is obtained as measured value, and the guided inflow and outflow of the fluid is continuously conducted in batches to continuously obtain signal values for averaging processing of plural data, so that affections by drift of reference point (zero point) due to moment-to-moment change and/or variation of offset (fluctuation) are consistently excluded and minute concentration of magnetic material in the drain oil can be measured continuously.

In the first embodiment, when the phase of the reference signal or the phase of the detection signal of magnetic material is set in the shifted manner to the other signal, amplification of the signal by the amplifier 18 or 25 can be further facilitated, so that minute concentration of magnetic material in the drain oil can be favorably measured. When the phase is shifted by 10°-170°, minute concentration of magnetic material can be measured; when the phase is shifted by 45°-135°, minute concentration of magnetic material can be favorably measured; and when the phase is shifted by about 90°, minute concentration of magnetic material can be extremely favorably measured.

In the first embodiment, when the phase of the reference signal or the phase of the detection signal of magnetic material is shifted and the value of the output signal of the signal processor (lock-in amplifier) 5 converted into DC voltage signal is made to approach zero with no magnetic material being detected, amplification of the signal can be facilitated, so that minute concentration of magnetic material in the drain oil can be favorably measured.

In the first embodiment, the detection means 3 comprises the detection coil 11b for obtaining detection signal of magnetic material and the exciting coils 11a, AC voltage being applied to the exciting coils 11a to generate the output signal indicative of AC voltage in the detection coil 11b; obtained from the output signal is the detection signal of magnetic material or the corrective detection signal while the reference signal is obtained, for example, from the oscillating circuit 14 connected to the exciting coils 11a, so that voltage and phase are varied by the AC voltage and depending on concentration of magnetic material. As a result, measurement of concentration of magnetic material is facilitated and minute concentration of magnetic material in the lubricant can be favorably measured. Because of using the exciting coils 11a, the reference signal can be easily prepared which has the same frequency relative to the output signal of the detection coil 11b.

In the first embodiment, when the detection means 3 comprises the plural exciting coils 11a wound inversely to each other and the detection coil 11b arranged between the exciting coils 11a such that the output signal of the detection coil 11b is small, concentration of magnetic material can be detected highly sensitively through the amplifier 18 or 25 so that minute concentration of magnetic material in drain oil can be measured with high accuracy.

In the first embodiment, when the inflow/outflow of the drain oil is guided by reciprocal movement of the piston 2a as inflow/outflow guide means 2, any accumulated solids can be readily discharged and measurement can be continuously conducted, so that minute concentration of magnetic material in the drain oil can be continuously measured with high accuracy with no measurement errors duce to disturbance or changes over time. Any accumulated solids are favorably removed by reciprocal movements of the piston 2a, which can make it unnecessary to use periodic air blowing or mechanical removal. Even if the drain oil has high viscosity, the inflow/outflow of the drain oil can be reliably guided in a predetermined interval by reciprocal movements of the piston 2a, so that concentration of magnetic material in the drain oil can be continuously measured with high accuracy.

In the first embodiment, when the signal processing unit 6 has the signal processor 5 for noise removal from the detection signal of magnetic material with the fluid being introduced and the corrective detection signal with the fluid being discharged, using the reference signal of the same frequency, the detection signal for magnetic material obtained from the drain oil in the detection unit 4 is noise-removed by the band-pass filter 13, and further noise removal is made by the signal processor 5 in combination with the reference signal of the same frequency. Then, the corrective detection signal obtained from the detection unit 4 with the drain oil being discharged is noise-removed by the signal processor 5 in combination with the reference signal, the difference between the respective detection signal values after conversion being used as concentration of magnetic material for the drain oil. Thus, noise superimposed on the output signal upon measurement is removed, so that minute concentration of magnetic material in the drain oil can be measured with high accuracy.

In the first embodiment, obtained from the fluid (test object) containing magnetic material is at least one of informations including concentration, rate of change in concentration, amplitude of variations of concentration, cycle of variations of concentration and concentration deflection in multipoint measurement of magnetic material, status of sliding parts being determined on the basis of preliminarily obtained correlationship between concentration of magnetic material and status of sliding parts, so that status monitoring and maintenance of the piston or other sliding parts and control of the drain oil (lubricating fluid) can be conducted extremely easily and accurately.

In the first embodiment, when a measured value indicating and abnormality determination device (alert means) 7 is provided which issues a warning or/and an alert depending on the status of the sliding parts, condition monitoring and maintenance of the sliding parts such as piston can be conducted extremely easily and speedy.

In the first embodiment, when depending upon status of the sliding parts, amount, timing, pressure, temperature and injection method of the drain oil (lubricating fluid) to be supplied to the sliding parts and properties of the lubricating fluid are controlled, sliding status of the sliding parts such as piston can be favorably maintained.

Figure 9:
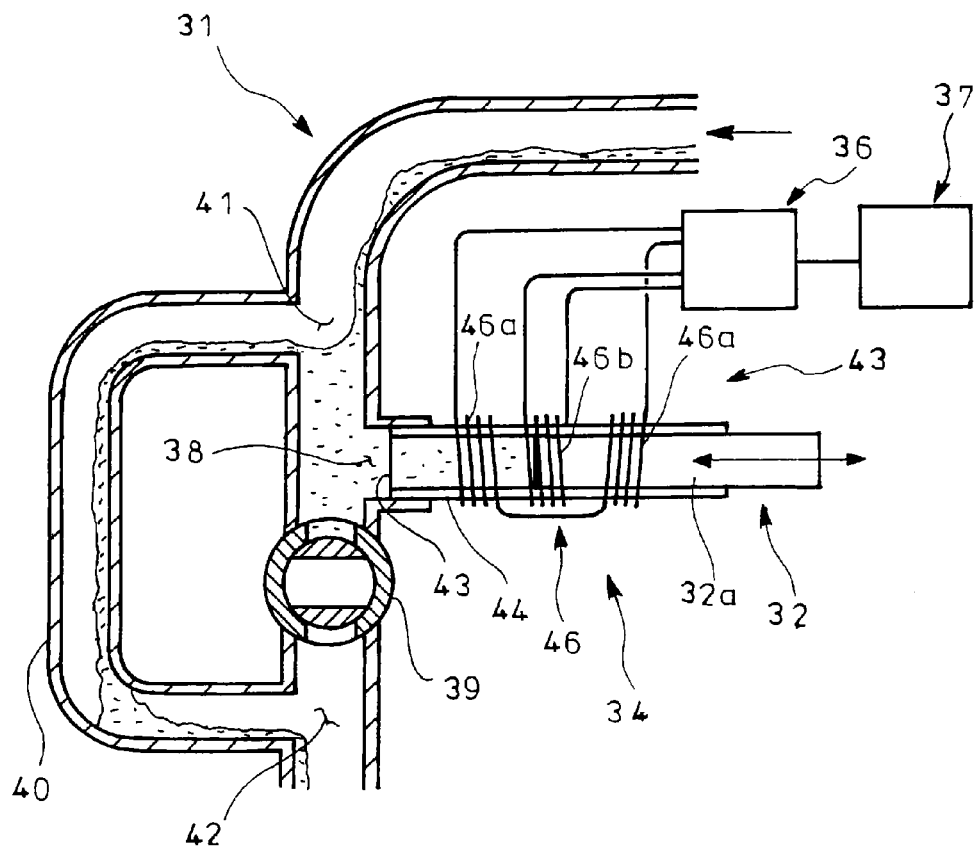
FIG. 9 is a schematic view showing a second embodiment of the invention.
Figure 10:
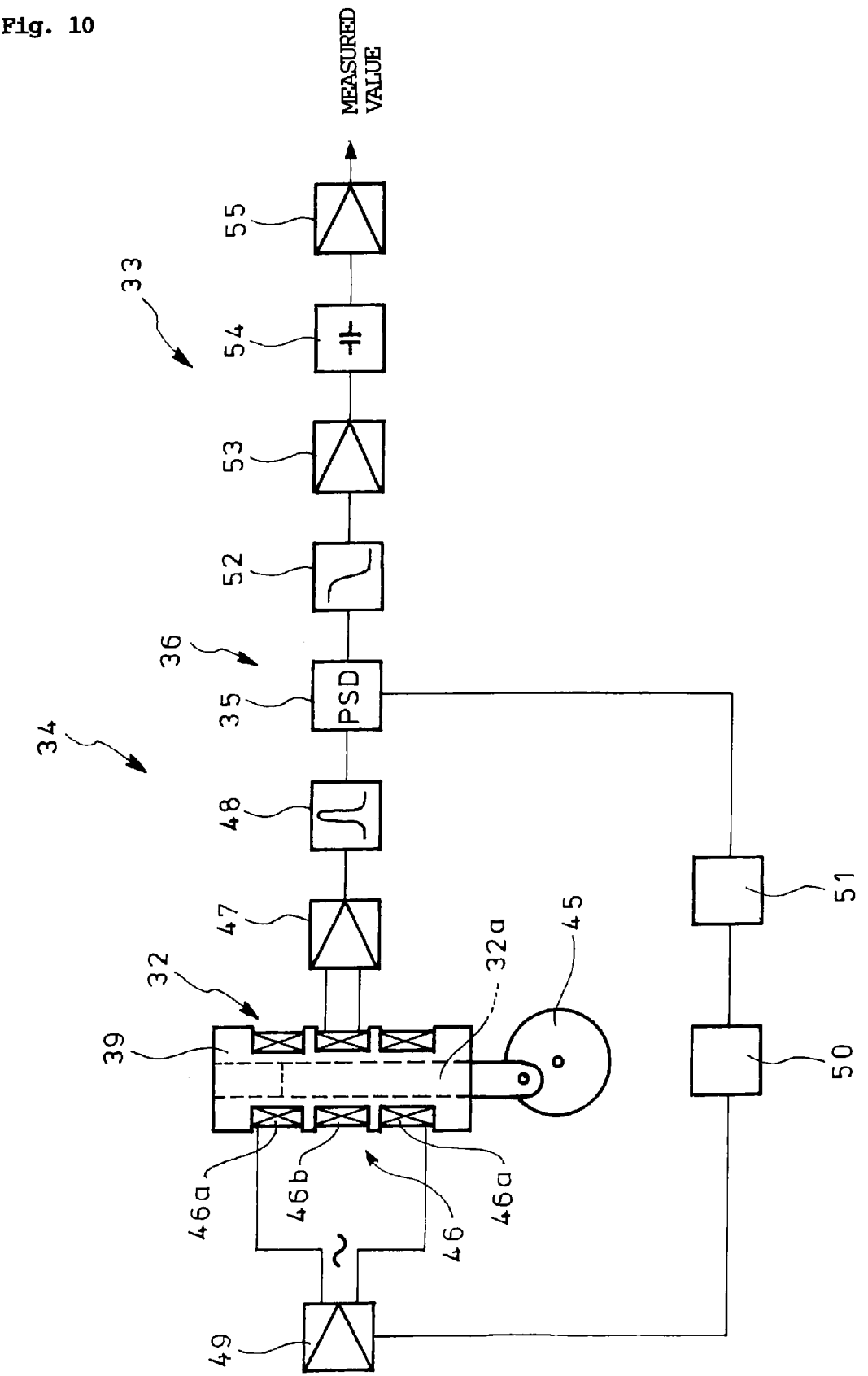
FIG. 10 is a block diagram showing inflow/outflow guide means and a signal processing unit according to the second embodiment.
Figure 11:
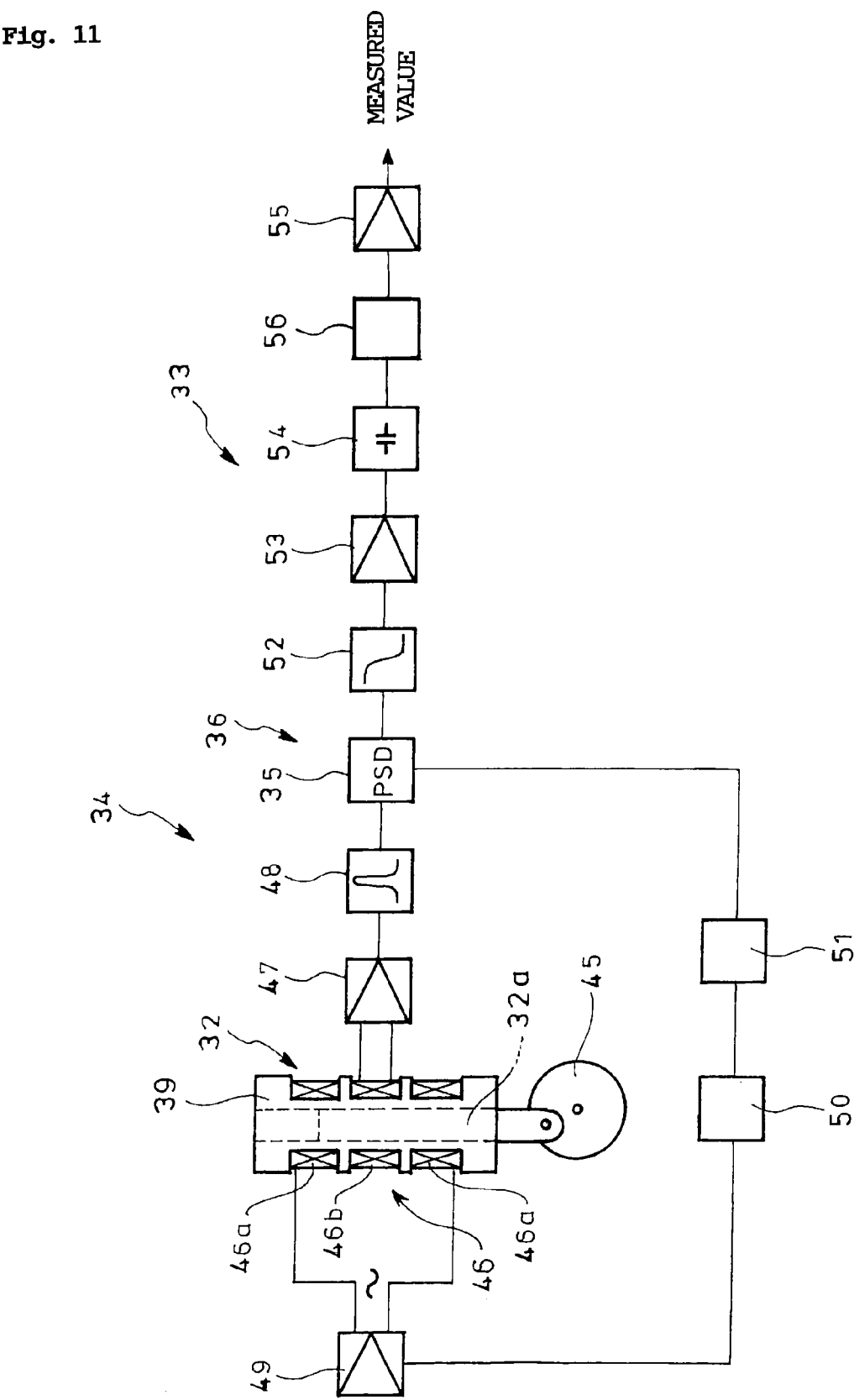
FIG. 11 is a block diagram showing the inflow/outflow guide means and a variation of the signal processing unit according to the second embodiment.

A device and a method for measuring a concentration of magnetic material of the second embodiment according to the invention will be described. FIGS. 9-11 show the second embodiment of the invention.

In the second embodiment, connected to a conduit passage 31 of flow of fluid such as drain oil containing magnetic material powder is a detection unit 34 comprising inflow/outflow guide means 32 and detection means 33. Connected to the detection means 33 of the detection unit 34 is a signal processing unit 36 with a lock-in amplifier 35 and the like, the signal processing unit 36 being connected to a measured value indicating and abnormality determination device 37.

The conduit passage 31 serves to discharge drain oil from an equipment (not shown) such as a diesel engine with a drive piston, a driven cylinder and the like. Arranged downstream of the passage 31 are an on-off valve 39 as shutoff means providing a pool 38 for the drain oil and a branch passage 40 for bypass of the on-off valve 39 and having a branch port 41 formed upstream of the pool 38 and a junction port 42 formed downstream of the on-off valve 39 to cause the drain oil overflowing from the pool 38 to flow downstream. The fluid is not limited to drain oil and may be any provided that it contains magnetic material.

The detection unit 34 comprises a cylindrical detection body 44 associated with the passage 31 at the pool 38 between the on-off valve 39 and the branch port 41 through an opening 43, a piston 32a as inflow/outflow guide means 32 sliding in the detection body 44, a rotary part 45 for reciprocating the piston 32a and a plurality of coils 46 of the detection means 33 arranged on an outer periphery of the detection body 44.

The plural coils 46 of the detection means 33 comprises two exciting coils 46a wound inversely and connected in series to each other and a detection coil 46b arranged between the two exciting coils 46a, an output signal indicative of AC voltage being generated in the detection coil 46b when AC voltage is applied to the exciting coils 46a, adjustment being made to make the output signal for the detection coil 46b small when no magnetic material being detected. The exciting and detection coils 46a and 46b are adjusted to have substantially uniform mutual inductance by adjusting wound number of and distance between the coils 46. It is preferable that the output signal for the detection coil 46b is adjusted to be small. The exciting and detection coils 46a and 46b have no limitation in their numbers. Preferably, a shield such as an aluminum cylinder is arranged outwardly of the coils 46 so as to prevent intrusion of any outside noises. Just like the first embodiment, the coils 46 may comprise an exciting coil and a detection coil (output coil) arranged adjacent to the exciting coil.

In order to obtain the detection signal of magnetic material or the corrective detection signal from the output signal of the detection coil 46b, the signal processing unit 36 comprises an amplifier circuit 47 connected to the detection coil 46b to amplify a faint wave signal, a band-pass filter 48 connected to the amplifier circuit 47 to remove noises of the wave signal in a predetermined range, a since wave oscillating circuit 49 connected to the exciting coils 46a to obtain sine wave for excitation, a phase circuit 50 connected to the sine wave oscillating circuit 49 to shift the phase of the sine wave for excitation and an edge-triggered circuit 51 connected to the phase circuit 50 to convert the sine wave for excitation into a rectangular wave. The phase circuit 50 may be alternatively positioned between the band-pass filter 48 and the lock-in amplifier 35 to shift not the reference signal but the detection signal for magnetic material and the corrective detection signal by about 90°. The phase circuit 50 preferably shifts the phase by 90° when no magnetic material is detected; the phase shift may be slightly over or below due to electric deviance. Alternatively, just like the first embodiment, the phase circuit 50 may shift the phase by 10°-170° with no magnetic material being detected.

The signal processing unit 36 comprises a lock-in amplifier connected to the band-pass filter 48 and to the edge-triggered circuit 51, a low-pass filter 52 connected to the lock-in amplifier 35 to convert the output signal into DC voltage signal, an amplifier 53 connected to the low-pass filter 52 to amplify the DC voltage signal, an AC signal transmission circuit 54 connected to the amplifier 53 and an amplifier 55 connected to the transmission circuit 54. A DC conversion circuit 56 for conversion of the AC signal in accordance with the movement of the piston 32a may be provided, as shown in FIG. 11, between the AC signal transmission circuit 54 and the amplifier 55 for facilitation of succeeding processing.

The measured value indicating and abnormality determination device 37 is connected to the amplifier 55 of the signal processing unit 36 for conversion of the signal into a value of concentration of magnetic material and can issue abnormality alert. As in the first embodiment, the measured value indicating and abnormality determination device 37 may have a controller (not shown) for predetermined controls to make, for example, lubrication control or issue of abnormality alter.

Mode of operation of the second embodiment according to the invention will be described.

When the concentration of magnetic material powder contained in the drain oil (fluid) is to be measured, preliminarily the piston 32a as inflow/outflow guide means 32 is pushed out in the detection unit 34 and the on-off valve 39 in the passage 31 is closed to pool a constant amount of drain oil in the pool 38. Then, the piston 32a as inflow/outflow guide means 32 is drawn to introduce the drain oil from the pool 38 into the detection unit 34 where the output signal is measurement processed with the drain oil being present. Preferably, the piston 32a as inflow/outflow guide means 32 is drawn to introduce the drain oil to an extent that the fluid reaches the one of the exciting coil 46a and a half of the detection coil 46b.

When the measurement processing is conducted with the drain oil being introduced in the detection unit 34 (i.e., during processing with the fluid being introduced), the detection signal for magnetic material is obtained ((A') in FIG. 6) from the drain oil in the detection unit 34 by the detection coil 46b, the amplifier circuit 47 and the band-pass filter 48 while preparing a reference signal ((B') in FIG. 6) which has the rectangular wave and which has the same frequency as that of the detection signal (exciting voltage) of magnetic material with a constant phase difference through shift of the phase with about 90° by the exciting coil 46a, the sine wave oscillating circuit 49, the phase circuit 50 and the edge-triggered circuit 51. Noise removal is conducted by the lock-in amplifier 35 in combination of the output signal of magnetic material with the reference signal with the same frequency and conversion is conducted by the low-pass filter 52 into plain DC voltage signal ((D') in FIG. 6) as output value for concentration of magnetic material and is inputted via the amplifier into the AC signal transmission circuit 54. (C') of FIG. 6 shows the detection signal for magnetic material with inversions by the reference signal, such areas being integration converted into (D') of FIG. 6.

Then, the piston 32a as inflow/outflow guide means 32 is pushed out to discharge (effect guided outflow of) the drain oil in the detection unit 34; then, the output signal with no drain oil being present (i.e., of the inflow/outflow guide means 32 itself) is measurement processed. Time interval of reciprocal movements of the inflow/outflow guide means 32, which may vary depending on for example viscosity of the fluid to be measured, is preferably several seconds.

When the measurement processing is conducted with the drain oil being discharged (guided to make outflow) out of the detection unit 34 (i.e., during processing with the fluid being discharged), the corrective detection signal is obtained ((A) in FIG. 5) from the detection unit 34 by the detection coil 46b, the amplifier circuit 47 and the band-pass filter 48 while preparing a reference signal ((B) in FIG. 5) which has the rectangular wave and which has the same frequency as that of the corrective detection signal (exciting voltage) with a constant phase difference through shift of the phase with about 90° by the exciting coil 46a, the sine wave oscillating circuit 49, the phase circuit 50 and the edge-triggered circuit 51. Noise removal is conducted by the lock-in amplifier 35 in combination of the corrective detection signal with the reference signal having the same frequency and conversion is conducted by the low-pass filter 52 into plain DC voltage signal ((D) in FIG. 5) as comparative output value and is inputted via the amplifier into the AC signal transmission circuit 54; (C) of FIG. 5 shows the detection signal for magnetic material with inversions by the reference signal, such areas being integration converted into (D) of FIG. 5.

In order to correct the output value for the concentration of magnetic material, by the AC signal transmission circuit 54, as shown in FIG. 6, difference $\Delta V$ is obtained from the output value for the concentration of magnetic material and the comparative output value and is converted into DC voltage signal, the difference being converted into a value of concentration of magnetic material by the measured value indicating and abnormality determination device 37, using preliminarily obtained correlationship (functional processing). As to the output value (DC voltage signal) for concentration of magnetic material and the comparative output value (DC voltage signal), phase difference $\Delta f$ between the output signal for magnetic material and the reference signal therefor and phase difference (not shown) between the corrective output signal and the reference signal therefor may be alternatively detected by the lock-in amplifier 35, the conversion being made depending upon the detected phase difference amount.

Then, the processing with the drain oil being introduced in the detection unit 34 (processing with the fluid being introduced) and the processing with the drain oil being discharged (guided for outflow) from the detection unit 34 (the processing with the fluid discharged) are alternately and continuously repeated by continuous reciprocal movements of the piston 32a as inflow/outflow guide means so that the difference signal is detected by the AC signal transmission circuit 54 and the like from the output value for concentration of magnetic material and the comparative output value, and moving average processing is conducted to obtain an average of the concentrations of magnetic material through the measured value indicating and abnormality determination device 37. The output values for concentration of magnetic material are, as shown in (D') in FIG. 6, AC signals which are above and below the comparative output value depending upon reciprocal movements of the inflow/outflow guide means. Such AC signals may be converted into DC signals, using the DC conversion circuit 56.

With the drain oil being measured, when the concentration of magnetic material powder exceeds a predetermined value and it is determined that the equipment with driving inflow/outflow guide means, drive cylinder and the like has considerably worn amount, the fact that it is time for maintenance required is notified to a manager by the measured value indicating and abnormality determination device 37 through warning display, alarm and/or hazard light. If the controller (not shown) is provided, just like the first embodiment, correlationship (reference data) between the status of the sliding parts such as piston and concentration of magnetic material may be compared with the informations obtained from the fluid (test object) including magnetic material, the sliding status of the sliding parts such as piston being determined to make control of the drain oil (lubricating fluid) to the sliding parts and issue of alarm or the like.

Thus, according to the second embodiment, the detection signal for magnetic material obtained from the drain oil in the detection unit 34 is noise-removed by the lock-in amplifier 35 in combination with the reference signal with the same frequency as that of the detection signal, conversion being made into DC voltage component part for concentration of magnetic material. Then, the corrective detection signal obtained from the detection unit 34 with the drain oil being discharged is noise-removed by the lock-in amplifier 35 in combination with the reference signal with the same frequency with that of the corrective detection signal and is converted into comparative DC voltage component part, the difference between the values of the respective DC component parts after conversion being used as the concentration of magnetic material for the drain oil. Thus, noise superimposed on the output signal upon measurement is removed, and the accumulated solid matters are discharged through the guided inflow/outflow of the drain oil by the inflow/outflow guide means, so that minute concentration of magnetic material in drain oil can be measured with high accuracy. The second embodiment utilizes, just like the first embodiment, phase difference generated between the voltages of the exciting and detection coils 46a and 46b, so that various variations can be comprehensively grasped such as variation in reactance of the exciting coil 46a depending on whether magnetic material is present or not, variation in reactance of the detection coil (output coil) 46b depending on whether magnetic material is present or not, variation of eddy current generated in the test object, variation in joule loss due to eddy current, variation in eddy current produced in objects surrounding the coil and variation in joule loss due to eddy current, and the concentration of magnetic material can be measured with high accuracy. For measurement of the concentration of magnetic material, when phase differences in part of variations were used among variations including variation in reactance of the exciting coil 46a depending on whether magnetic material is present or not, variation in reactance of detection coil (output coil) 46b depending on whether magnetic material is present or not, variation in eddy current generated in the test object, variation in joule loss by eddy current, variation in eddy current generated in objects surrounding the coil and variation in joule loss by eddy current, affections would be caused by the remaining variations unlike the case of phase difference of voltages, failing in measurement of the concentration of magnetic material with high accuracy.

The concentration of magnetic material is obtained as respective DC component in a batch of guided inflow and outflow of the drain oil, and the guided inflow and outflow of the drain oil is repeatedly conducted in plural batches to obtain differences of the respective DC component parts, so that plural data are averaging processed to consistently exclude affections by drift of reference point (zero point) due to changes over time and/or offset (fluctuation), and minute concentration of magnetic material in drain oil can be continuously measured.

In the second embodiment, the detection signal for magnetic material with the drain oil being introduced and the corrective detection signal with the drain oil being discharged are obtained from the output signal indicative of AC voltage, phase differences between the respective signals and the reference signals are detected by the lock-in amplifier 35 and conversion is made into signal depending upon detected phase difference amount, even with slight phase difference, concentration of magnetic material is detected with high sensitivity, so that minute concentration of magnetic material in drain oil can be favorably measured with high accuracy.

In the second embodiment, when the phase of the reference signal or the phase of the detection signal for magnetic material is shifted to make the value for the output signal of the lock-in amplifier 35 converted into DC voltage signal to approach zero with no magnetic material being detected, amplification of the signal can be easily conducted, so that minute concentration of magnetic material in drain oil can be favorably measured.

In the second embodiment, when the phase of the reference signal or the phase of the detection signal for magnetic material is shifted by about 90° relative to the other signal, amplification of the signal by the amplifiers 53 and 55 can be further easily conducted, so that minute concentration of magnetic material in drain oil can be extremely favorably measured.

In the second embodiment, when the detection means comprises the detection coil 46b for obtaining the detection signal for magnetic material and the exciting coil 46a, the output signal for AC voltage being generated in the detection coil 46b when AC voltage is applied to the exciting coil 46a, the detection signal of magnetic material or the corrective detection signal being obtained from the output signal, the reference signal being obtained from the oscillating circuit 49 and the like connected to the exciting coil 46a, then, the voltage and phase are varied by the AC voltage and depending on the concentration of magnetic material, which facilitates measurement of the concentration of magnetic material, so that minute concentration of magnetic material in drain oil can be favorably measured. Because of using the exciting coil 46a, the reference signal may be readily prepared which has the same frequency relative to the output signal of the detection coil 46b.

In the second embodiment, when the detection means comprises the plural exciting coils 46a wound inversely to each other and the detection coil 46b arranged between the exciting coils 46a such that the output signal for the detection coil 46b is small, the concentration of magnetic material is measured highly sensitively through the amplifiers 53 and 55, so that minute concentration of magnetic material in drain oil can be measured with high accuracy.

In the second embodiment, when inflow/outflow of the drain oil is guided by the reciprocal movements of the piston 32a as inflow/outflow guide means, the accumulated solid matters are readily discharged and the measurement can be conducted continuously with disturbance and changes over time being eliminated, so that minute concentration of magnetic material in drain oil can be continuously measured with high accuracy. The accumulated solid matters and the like are favorably discharged through reciprocal movements of the piston 32a, which can make it unnecessary to use periodic air blowing or mechanical removal. Even if the drain oil has high viscosity, the inflow/outflow of the drain oil can be reliably guided by the reciprocal movements of the piston 32a at a constant interval, so that concentration of magnetic material in drain oil can be continuously measured with high accuracy. Further, the second embodiment has effects and advantages substantially similar to those of the first embodiment.

Figure 12:
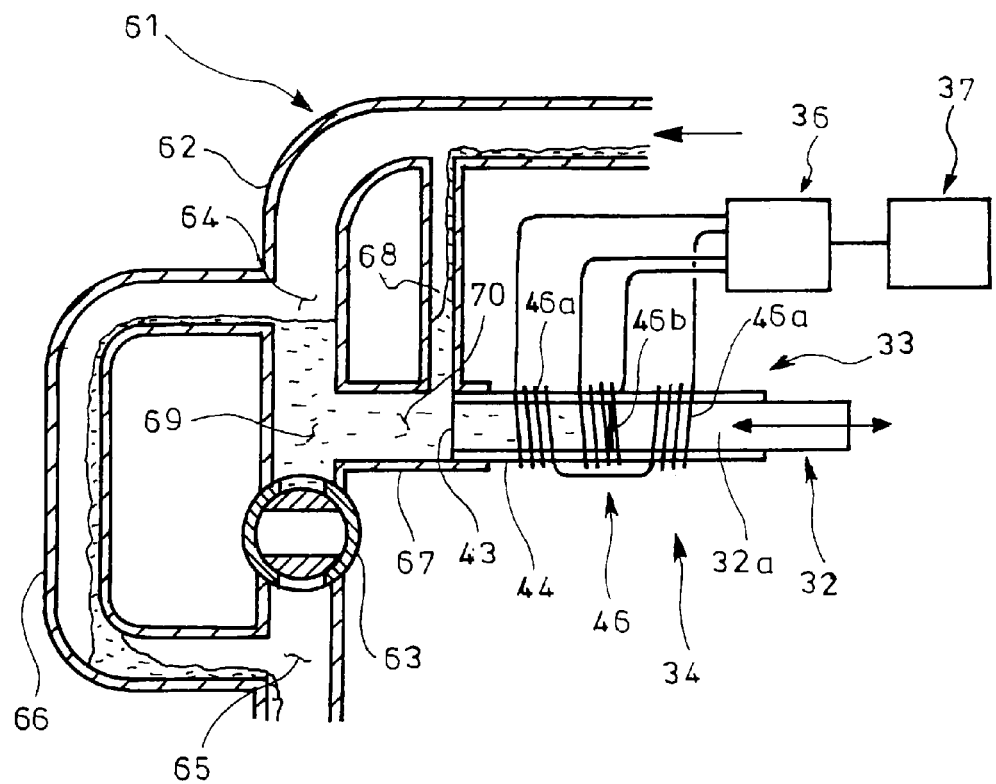
FIG. 12 is a schematic view showing a third embodiment of the invention.

Next, a device for measuring a concentration of magnetic material according to a third embodiment of the invention will be described. FIG. 12 shows the third embodiment of the invention. In the figure, parts similar to those in FIG. 9 are represented by the same reference numerals.

The third embodiment has a conduit passage 61 of flow of fluid such as drain oil which is a variation of the conduit passage 31 in the second embodiment and to which is connected a detection unit 34 substantially similar to that of the first embodiment.

The conduit passage 61 of the third embodiment serves to discharge drain oil from equipment such as a diesel engine (not shown) with a drive piston, a drive cylinder and the like. Arranged downstream of the passage 61 are a main passage 62 with a curve extending from horizontal to vertical, an on-off valve 63 as shutoff means arranged in the vertical portion of the main passage 62, a branch passage 66 with branch and junction ports 64 and 65 for bypassing of the on-off valve 63 substantially like the first embodiment, an extension passage 67 between the on-off valve 63 and the branch port 64 and extending horizontally in a predetermined length and a small-diameter communication passage 68 which connects an end of the extension passage 67 with a horizontal portion of the main passage 62.

A portion of the main passage 62 between the branch port 64 and the on-off valve 63 as shutoff means serves as a first pool 69 for pooling of old fluid or drain oil, and a extension passage 67 and a communication passage 68 serve as a second pool 70 for receiving and pooling of new fluid or drain oil. The branch passage 66 serves to cause, like the first embodiment, the drain oil overflowing from the first pool 69 to flow downstream. The communication passage 68 is arranged such that the drain oil first flows into the passage prior to the vertical portion of the main passage 62.

The detection unit 34 comprises a cylindrical detection body 44 with an opening 43 open to the second pool 70 at a juncture between the extension passage 67 and the communication passage 68, a piston 32a as inflow/outflow guide means 32 sliding in the detection body 44, drive means (not shown) for driving the piston 32a as inflow/outflow guide means 32, a plurality of coils 46 of detection means 33 arranged on an outer periphery of the detection body 44, a signal processing unit 36 for the detection means 33 for controlling the signal of the coils 46 and a measured value indicating and abnormality determination device 37 connected to the signal processing unit 36. The detection body 44 of the detection unit 34 is arranged to extend from the extension passage 67 so as to enhance reliability of the guided inflow/outflow of the fluid.

Mode of operation of the third embodiment according to the invention will be described.

When concentration of magnetic material powder contained in the drain oil is to be measured, preliminarily with the piston 32a as inflow/outflow guide means 32 in the detection unit 34 being pushed out, the on-off valve 63 in the conduit main passage 62 is closed to pool a predetermined amount of drain oil in the first and second pools 69 and 70. By the inflow/outflow guide means 32, the inflow/outflow of the drain oil in the second pool section 70 is guided for measurement of the concentration of magnetic material substantially like the first embodiment.

Thus, according to the third embodiment, effects and advantages can be obtained which are substantially similar to those in the first embodiment. In the third embodiment, the pool comprises a first pool 69 for storage of old fluid and a second pool 70 for reception and storage of new fluid. With the detection unit 34 being connected to the second pool 70, new fluid or drain oil is introduced into the detection unit 34 by the inflow/outflow guide means 32, so that mixing of old fluid with the new fluid is prevented and concentration of magnetic material in fluid can be continuously measured with high accuracy. Arrangement of the detection unit 34 and the first and second pools 69 and 70 favorably prevent any air from being mixed into the fluid, so that concentration of magnetic material powder in fluid can be continuously measured with extremely high accuracy.

It is to be understood that a device and a method for measuring a concentration of magnetic material according to the invention are not limited to the above-mentioned embodiments and that various changes and modifications may be made without departing from the scope of the invention. For example, any structure and signal processing other then those of the embodiments may be used provided that concentration of magnetic material is continuously measured with affections by disturbances and changes over time being eliminated. The fluid is not limited to drain oil and may be other oil, an aqueous solution, water or powder. Any processing means may be utilized provided that it can obtain difference in signal between the processing with no fluid being introduced and the processing with the fluid being discharged. The inflow/outflow guide means may be an eccentric rotator in place of the piston.

INDUSTRIAL APPLICABILITY

A device and a method for measuring a concentration of magnetic material according to the invention can measure a concentration of magnetic material owing to sliding of parts.

The invention claimed is:

1. A device for measuring a concentration of magnetic material comprising a detection unit connected to a passage of flow of or a pool for pooling of fluid containing magnetic material and having inflow/outflow guide means and detection means, and a signal processing unit connected to said detection means and having a lock-in amplifier, said detection unit guiding inflow/outflow of the fluid by means of the inflow/outflow guide means and obtaining a detection signal of magnetic material with the fluid being introduced and a corrective detection signal with the fluid being discharged from an output signal indicative of AC voltage through the detection means, said signal processing unit employing reference signals with the same frequencies as those of the respective signals to noise-remove said respective signals through the lock-in amplifier and detecting phase differences between said respective signals and the reference signals to thereby conduct conversion into DC voltage signals depending on detected phase difference amount, difference of respective values after conversion being detected as concentration of magnetic material.

2. A device for measuring concentration of magnetic material as claimed in claim 1, wherein said signal processing unit shifts the phase of the reference signal or the detection signal of magnetic material such that value of the output signal converted into DC voltage signal approaches substantially zero when no magnetic material is detected.

3. A device for measuring a concentration of magnetic material as claimed in claim 1, wherein said detection means comprises an exciting coil and an output coil for obtaining detection signal of magnetic material, the output signal for AC voltage being generated in the output coil by application of AC voltage to said exciting coil, a detection signal for magnetic material or a corrective detection signal being obtained from said output signal, reference signal being obtained from an oscillating circuit connected to said exciting coil.

4. A device for measuring a concentration of magnetic material as claimed in claim 1, wherein said detection means comprises a plurality of exciting coils wound inversely to each other, a detection coil being arranged between the plural exciting coils such that an output signal of said detection coil is small.

5. A device for measuring a concentration of magnetic material as claimed in claim 1, wherein said inflow/outflow guide means guides inflow/outflow of the fluid through reciprocal movements of the piston.

6. A device for measuring a concentration of magnetic material comprising a detection unit connected to a passage of flow of or a pool for pooling of fluid containing magnetic material and having inflow/outflow guide means and detection means and a signal processing unit connected to said detection means and having a lock-in amplifier, said detection unit guiding inflow/outflow of the fluid through the inflow/outflow guide means and obtaining a detection signal of magnetic material with the fluid being introduced and a corrective detection signal with the fluid being discharged through the detection means, said signal processing unit using reference signals of the same frequencies as those of the respective signals to conduct noise removal of said respective signals through the lock-in amplifier and then conducting conversion into DC voltage signals, difference of the respective values after conversion being detected as concentration of magnetic material.

7. A method for measuring a concentration of magnetic material comprising
processing with fluid being introduced wherein the fluid is introduced from a passage of flow of or a pool for pooling of fluid containing magnetic material into a detection unit and a detection signal is obtained from the fluid in the detection unit while preparing a reference signal with the same frequency as that of the detection signal, noise removal being conducted by a lock-in amplifier where the detection signal for magnetic material is combined with the reference signal with the same frequency, conversion being conducted into DC voltage signal as output value for concentration of magnetic material, processing with the fluid being discharged wherein a corrective detection signal is obtained from the detection unit with the fluid being discharged therefrom while the reference signal of the same frequency as that of the corrective detection signal is prepared, noise removal being conducted by the lock-in amplifier with the corrective detection signal being combined with the reference signal of the same frequency, conversion being conducted into DC voltage signal as comparative output value, said output value for concentration of magnetic material being corrected by said comparative output value.

8. A method for measuring a concentration of magnetic material as claimed in claim 7, wherein during processing with the fluid being introduced and processing with the fluid being discharged, detection signal for magnetic material and corrective detection signal are obtained from output signal indicative of AC voltage, noise removal being conducted by the lock-in amplifier from said respective signals with the detection signal for magnetic material and the corrective detection signal and the reference signals of the same frequency being combined together while phase differences between said respective signals and the reference signals are detected, conversion being conducted into output value for concentration of magnetic material and comparative output value depending on detected phase difference amount.

9. A method for measuring a concentration of magnetic material as claimed in claim 7, wherein the processing with the fluid being introduced and the processing with the fluid being discharged are alternately and continuously repeated so that difference is further converted into DC voltage signal from the output value for concentration of magnetic material and the comparative output value, said difference being converted into concentration of magnetic material by preliminarily obtained correlationship to eliminate measurement errors due to disturbance and changes over time.

10. A method for measuring a concentration of magnetic material as claimed in claim 7, wherein the phase of said reference signal or the phase of the detection signal for magnetic material is shifted and the value of an output signal of a signal processor converted into DC voltage signal is made to approach zero.

11. A method for measuring a concentration of magnetic material as claimed in claim 7, wherein obtained from a test object or fluid containing magnetic material is at least one of informations including concentration, rate of change in concentration, amplitude of variations of concentration, cycle of variations of concentration and concentration deflection in multipoint measurement of magnetic material, status of sliding parts being determined on the basis of preliminarily obtained correlationship between concentration of magnetic material and status of sliding parts.

12. A method for measuring a concentration of magnetic material as claimed in claim 11, wherein a warning or/and an alert is issued depending on status of the sliding parts.

13. A method for measuring a concentration of magnetic material as claimed in claim 11, wherein, depending on status of the sliding parts, amount, timing, pressure, temperature and/or injection method of lubricating fluid to be supplied to the sliding parts and/or properties of the lubricating fluid are controlled.

* * * * *